United States Patent
Kienzler et al.

(10) Patent No.: US 11,183,270 B2
(45) Date of Patent: Nov. 23, 2021

(54) NEXT GENERATION SEQUENCING SORTING IN TIME AND SPACE COMPLEXITY USING LOCATION INTEGERS

(71) Applicant: International Business Machines Corporation, Armonk, NY (US)

(72) Inventors: Romeo Kienzler, Allschwil (CH); Jenny Li, Cary, NC (US); Stefan Mueck, Cologne (DE); Stefan Ravizza, Wallisellen (CH)

(73) Assignee: International Business Machines Corporation, Armonk, NY (US)

( * ) Notice: Subject to any disclaimer, the term of this patent is extended or adjusted under 35 U.S.C. 154(b) by 793 days.

(21) Appl. No.: 15/834,302

(22) Filed: Dec. 7, 2017

(65) Prior Publication Data
US 2019/0180001 A1    Jun. 13, 2019

(51) Int. Cl.
*G16B 30/00* (2019.01)
*G06F 7/08* (2006.01)
(Continued)

(52) U.S. Cl.
CPC ............... *G16B 30/00* (2019.02); *G06F 7/08* (2013.01); *G16B 30/10* (2019.02); *G16B 30/20* (2019.02);
(Continued)

(58) Field of Classification Search
CPC .......... G06N 20/00; G06N 5/046; G06N 3/02; G06N 3/0472; G06N 7/005; G06N 5/003;
(Continued)

(56) References Cited

U.S. PATENT DOCUMENTS 7,962,489 B1* 6/2011 Chiang ................. G16B 30/10
707/741
9,235,680 B2* 1/2016 Rooyen ................. H01L 23/528
(Continued)

FOREIGN PATENT DOCUMENTS

WO    2017004589    1/2017

OTHER PUBLICATIONS

Liao et al. FeatureCounts: an efficient general purpose program for assigning sequence reads to genomic features. Bioinformatics (2014) vol. 30, No. 7 p. 923-930.*
(Continued)

*Primary Examiner* — Jesse P Frumkin
(74) *Attorney, Agent, or Firm* — Gilbert Harmon, Jr.; Aaron N. Pontikos

(57) ABSTRACT

A system and machine-implemented method for sorting Next-Generation Sequencing (NGS) reads in O(n) time and space complexity that makes use low sparsity and nearly uniform distribution of the input array. The genome position field in the input array is used to determine the target position of the output array. Duplicate target positions due to n-fold coverage are handled by assigning either overflow buckets to each position or anterior assigning multiple target slots in the output array for each genome position depending on the distribution of reads over the genome and the resulting probability of hitting an already occupied slot. Once every tuple in the input array has been written to the output array, the output array in read through ascending order and each tuple is appended to the end of a final result array.

17 Claims, 2 Drawing Sheets

(51) Int. Cl.
  *G16B 30/10* (2019.01)
  *G16B 30/20* (2019.01)
  *G16B 50/30* (2019.01)

(52) U.S. Cl.
  CPC ....... *G16B 50/30* (2019.02); *C12Q 2535/122* (2013.01)

(58) Field of Classification Search
  CPC .......... G06N 20/10; G06N 3/08; G06N 5/025; G06N 5/04; G06N 3/04; G06N 5/02; G05B 2219/32287; G05B 2219/35001; G05B 2219/40115; G05B 23/0221; G05B 23/0229; G05B 23/024; G05B 13/024; G05B 13/04; G06K 9/6263; G06K 9/00288; G06T 1/20; G06T 2207/20048; G06T 2207/20081; G06T 2207/20084; G06T 3/0006; G06T 7/32; G16B 20/00; G16B 45/00; G16B 50/00; G16B 40/00; G16B 30/00; G16B 30/10; G16B 20/20; G16B 40/20; G16B 5/00; G16B 25/00; G16B 35/00; G16B 50/10; G16B 50/30; G16B 5/10; G16B 5/20; G16B 99/00; G16B 10/00; G16B 40/10; G16B 50/50; G06F 16/9535; G06F 16/248; G06F 16/285; G06F 16/21; G06F 16/2264; G06F 16/245; G06F 16/2458; G06F 9/50; G06F 9/5072; G06F 9/5083; G06F 11/0709; G06F 11/1453; G06F 16/221; G06F 16/2462; G06F 16/2465; G06F 3/0641; G06F 11/3034; G06F 16/1748; G06F 2009/45583; G06F 2201/80; G06F 2212/401; G06F 3/061; G06F 3/0623; G06F 17/16; G06F 16/2255; G06F 2212/657; G06F 40/30; G06F 12/0261; G06F 16/2228; G06F 16/2455; G06F 16/31; G06F 16/35; G06F 16/901; G06F 16/90344; G06F 17/18; G06F 30/20; G06F 16/906; G06F 16/909; G06F 17/10; G06F 17/14; G06F 17/17; G06F 2111/10; G06F 7/00; G06F 7/36; G06F 7/722; G06F 7/06; G06F 7/10; G06F 7/12; G06F 7/22; G06F 7/24; G06F 7/08; G16H 50/20; G16H 15/00; G16H 10/40; G16H 10/60; G16H 40/63; G16H 40/67; G16H 50/70; G16H 20/30; G16H 50/50; G01N 2035/00881; G01N 2035/0091; G16C 20/60; H03M 13/6502
  See application file for complete search history.

(56) References Cited

U.S. PATENT DOCUMENTS

| | | | | |
|---|---|---|---|---|
| 9,663,826 | B2 | 5/2017 | Barrett et al. | |
| 9,734,284 | B2 | 8/2017 | Olson | |
| 10,930,369 | B1* | 2/2021 | Blattner | G16B 30/00 |
| 2008/0256070 | A1* | 10/2008 | Inglis | G16B 50/00 |
| 2014/0297196 | A1* | 10/2014 | Olson | G16B 30/00 |
| | | | | 702/19 |
| 2016/0244827 | A1* | 8/2016 | Turk | C12Q 1/6809 |
| 2016/0246871 | A1* | 8/2016 | Singh | G06F 16/285 |
| 2016/0259886 | A1* | 9/2016 | Li | G16B 30/00 |
| 2016/0291942 | A1* | 10/2016 | Hutchison | G06F 8/34 |
| 2017/0169159 | A1* | 6/2017 | Sazonov | G16B 30/00 |
| 2018/0247012 | A1* | 8/2018 | Verzotto | G16B 30/00 |
| 2019/0026156 | A1* | 1/2019 | Lu | C12Q 1/686 |
| 2019/0087601 | A1* | 3/2019 | Molyneaux | G16B 50/00 |
| 2019/0370254 | A1* | 12/2019 | Maxwell | G16B 5/10 |
| 2020/0104464 | A1* | 4/2020 | Kaufman | G16B 30/00 |

OTHER PUBLICATIONS

Santana-Quintero et al. Hive-Hexagon: high performance, parallelized sequence alignment for next generation sequencing data analysis. PLOSONE (2014) vol. 9 issue 6 e99033.*

Tischler et al. (2014) biobambam: tools for read pair collation based algorithms on BAM files. Source code for Biology and Medicine vol. 9 No. 13, 18 pages.*

Baichoo et al. Computational complexity of algorithms for sequence comparison, short read assembly and genome alignment. (Apr. 6, 2017) BioSystems vol. 156-157 pp. 73-85.*

Canzar et al. Short Read Mapping: an algorithmic tour. (Mar. 3, 2017) Proceedings of the IEEE vol. 105 No. 3 pp. 436-456.*

Baichoo, S. et al. Computational complexity of algorithms for sequence comparison, short-read assembly and genome alignment. (Apr. 2017) BioSystems, vols. 156-157, pp. 72-85. (Year: 2017).*

Belazzougui et al. Linear-time string indexing and analysis in small space. (deposited Sep. 20, 2016) arXiv 1609:06378v1. (Year: 2016).*

Crochemore, M. Computing the Burrows-Wheeler transform in place and in small space. (2015) Journal of Discrete Algorithms vol. 32, pp. 44-52. (Year: 2015).*

Louza et al. Burrows-Wheeler transform and LCP array construction in constant space. (2017, published online Nov. 22, 2016) Journal of Discrete Algorithms vol. 42 pp. 14-22. (Year: 2017).*

* cited by examiner

NEXT GENERATION SEQUENCING SORTING IN TIME AND SPACE COMPLEXITY USING LOCATION INTEGERS

BACKGROUND

The present invention relates to next generation sequencing and, more specifically, to a next generation sequencing platform using a transition function based approach to improve throughput and speed.

Next-generation sequencing (NGS), also known as high-throughput sequencing, is a phrase used to describe a number of different modern sequencing technologies that allow for the sequencing of DNA or RNA. NGS platforms perform sequencing of millions of small fragments of DNA in parallel, thereby creating a massive pool of data. For example, the genome is fragmented into pieces of 50-500 base pairs length each and digitalized through the NGS sequencer, which can result in up to 100 giga base-pairs (Gb) of raw sequencer output. Bioinformatics analysis algorithms are then employed to re-sequence the data by aligning the sequenced fragments against a reference genome for further analysis, such as the identification of unexpected variations in genes.

In a conventional NGS process, the alignment of the sequencing data against the reference genome can be difficult due to the presence of both expected and unexpected mutations in the sequencing data. These variations can hinder the process of identifying the correct position of the sequences fragments with respect to the reference genome. While there are existing sorting algorithms that may used to help align the sequenced fragments, these approaches do not take into account the special characteristics of the sequence data or its distribution and are thus not as efficient as possible. Accordingly, there is a need in the art for an NGS platform that can more align sequences fragments to a reference genome more accurately and efficiently.

SUMMARY

According to an embodiment, improved alignment may be accomplished with a platform for performing next generation sequencing (NGS) that takes into account the non-sparsity and the known distribution of positions of the fragment data. An empty target array may be allocated either in main memory or on persistent storage and its estimated size can be derived from the input array. The input array may then be read through a transition function, as further described below, that determines the position in the output array that the tuple is written to. If a target slot is already taken, subsequent target slots for the same position will be used until all are depleted and then an overflow bucket is used. The number of necessary slots per genome position can be derived empirically from similar experiments. As a final step, the target array is read in ascending order and each tuple is appended to the final result array which has thus been sorted in O(n) time and space complexity.

In another embodiment, a system for aligning genomic sequence data to a reference may be used that has a processor programmed to receive an input array comprising a plurality of fragments and align the plurality of fragments against a reference using a location integer, wherein the processor is programmed to sort the plurality of fragments in time complexity and space complexity. The processor may be programmed to determine the number of duplicate positions before sorting the plurality of fragments. The processor may be programmed to define an output array having a size equal to the number of fragments to be sorted multiplied by the number of duplicate positions. The processor may be programmed to estimate the number of duplicate position if a statistical distribution of duplicate positions is not uniform.

In a further embodiment, a method of aligning genomic sequence data to a reference may use a processor to receive an input array comprising a plurality of fragments and aligns the plurality of fragments against a reference using a location integer by sorting the plurality of fragments in time complexity and space complexity. The method may include determining the number of duplicate positions before sorting the plurality of fragments. The method may also include defining an output array having a size equal to the number of fragments to be sorted multiplied by the number of duplicate positions. The method may further include estimating the number of duplicate position if a statistical distribution of duplicate positions is not uniform.

In yet another embodiment, a computer program product for aligning genomic sequence data to a reference may be used where the computer program product comprises a computer readable storage medium having program instructions embodied therewith, the program instructions executable by a computing device to cause the computing device to receive an input array comprising a plurality of fragments and align the plurality of fragments against a reference using a location integer by sorting the plurality of fragments in time complexity and space complexity. The computer program product may additionally include program instructions that further cause the computing device to determine the number of duplicate positions before sorting the plurality of fragments. The computer program product may additionally include program instructions that further cause the computing device to define an output array having a size equal to the number of fragments to be sorted multiplied by the number of duplicate positions. The computer program product may further include program instructions that further cause the computing device to estimate the number of duplicate position if a statistical distribution of duplicate positions is not uniform.

DETAILED DESCRIPTION

Figure 1:
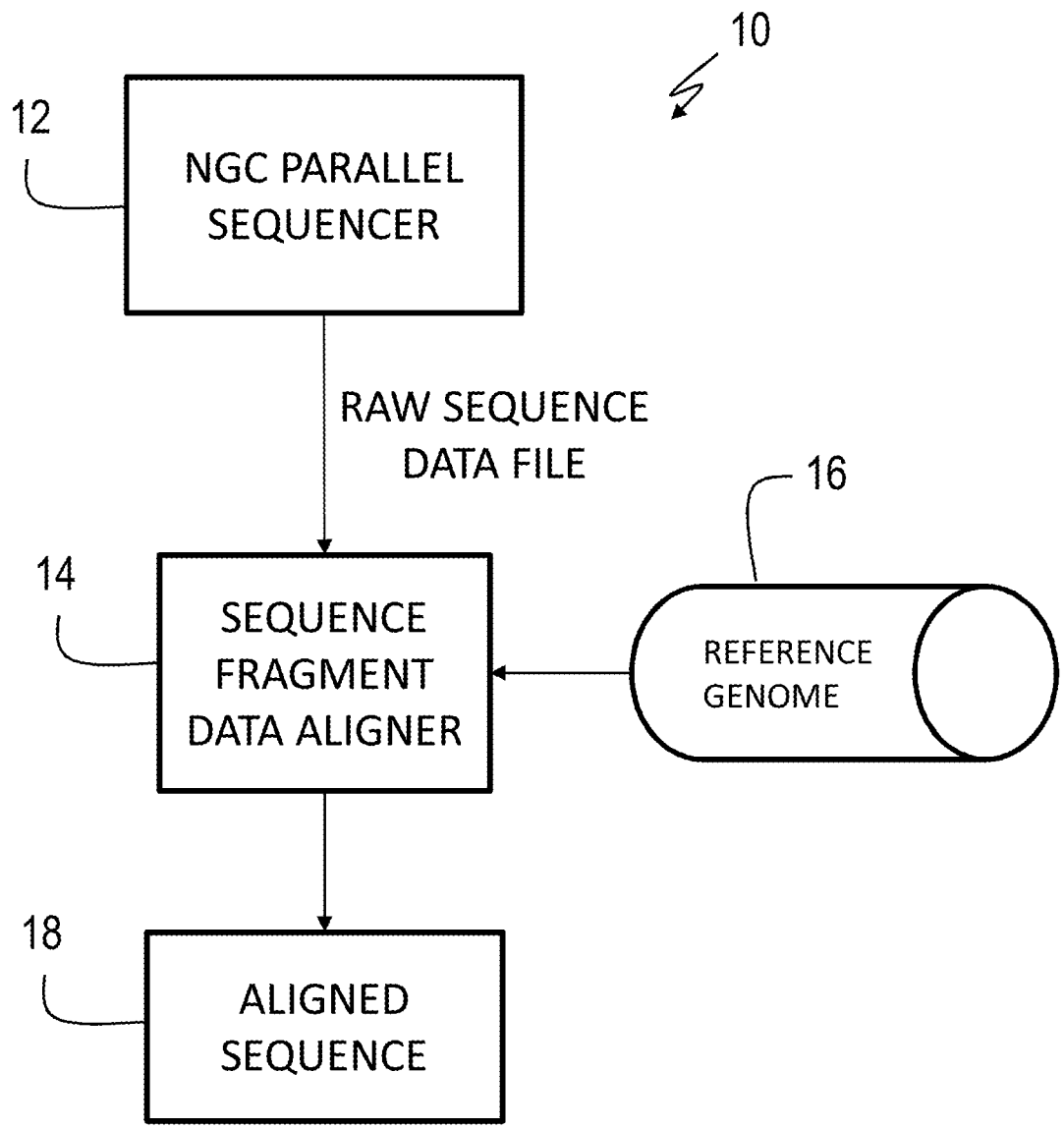
FIG. 1 is schematic of a system for aligning next generation sequence data against a reference genome.
Figure 2:
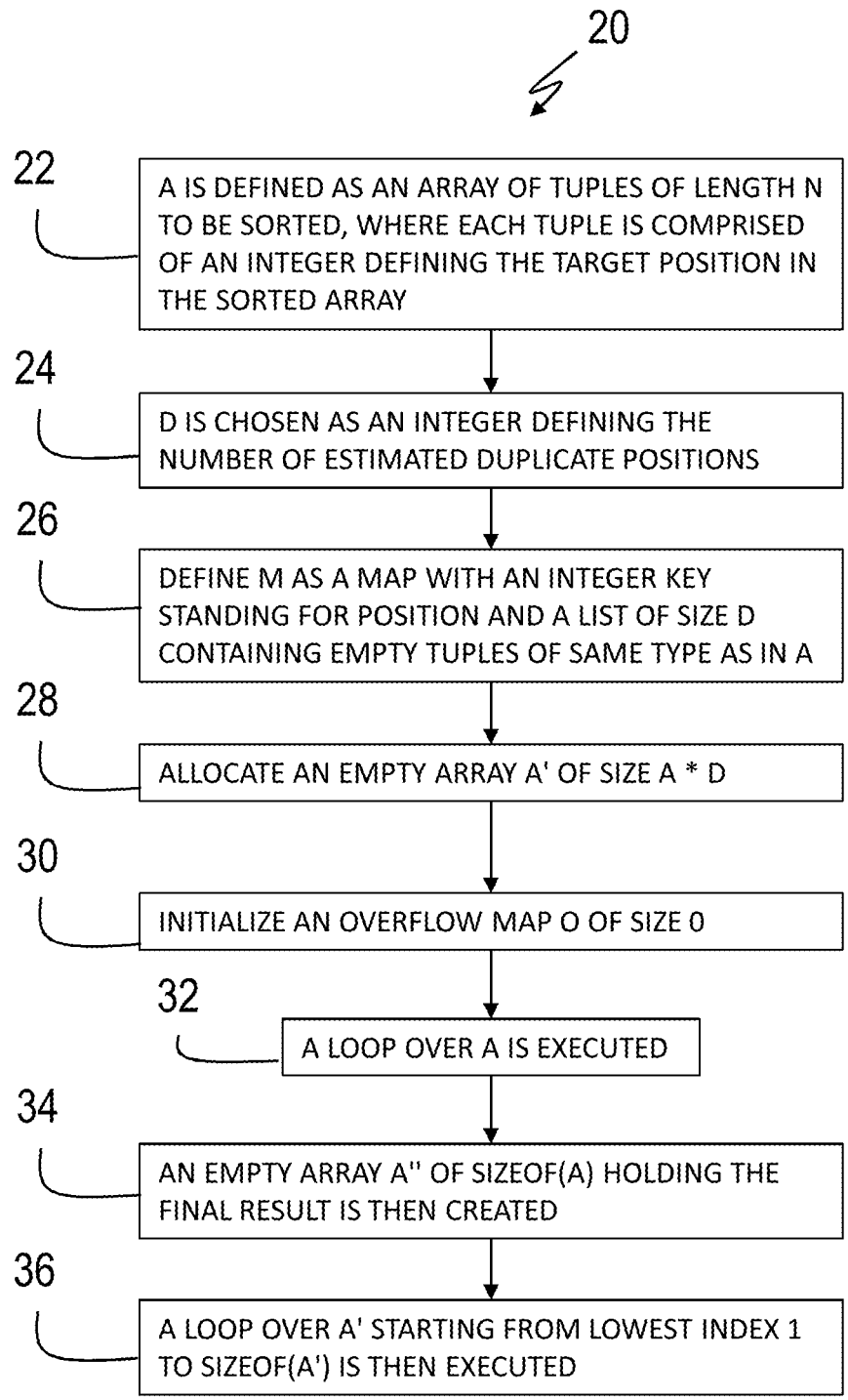
FIG. 2 is a flowchart of a method of aligning next generation sequence data against a reference genome.

Referring to the figures, wherein like numerals refer to like parts throughout, there is seen in FIG. 1, a system 10 for sorting next generation sequencing (NGS) fragment data. Fragment data is generated by a parallel sequencer 12 that sequences the DNA or RNA in a genetic sample from a target subject, such as human tissue sample. Parallel sequencer 12 output as a raw sequence fragment data file that contains data representing a plurality of fragments of the DNA or RNA that have been sequenced (typically 50 to 500 base pairs in length each) but are not arranged in the appropriate order reflecting the actual genome of the subject under evaluation. A sequence fragment data aligner 14 uses a reference genome 16 to align the fragment data into the appropriate positions to form an aligned sequence 18 so that it can be further analyzed, such as by looking for mutations within aligned sequence 18 that correspond to known gene locations in the reference genome 16. The alignment process involves two steps. First, the location of each fragment in the reference genome must be identified. Next, the fragments must be reassembled according to the determined locations to recreate the genome (or target genome region) of subject under evaluation.

More specifically, sequence fragment data aligner 14 includes a computer or processor that is programmed to receive as an input array the results of the sequencing of the small DNA or RNA fragments such as the raw sequence data file. For example, input array may comprise data configured in the FASTQ format, which is recognized as a de facto standard and into which virtually any other format may be easily converted. Sequence fragment data aligner 14 compares the raw sequence data file in the input array against reference genome 16 to assigns a genome position to each fragment. The fragments must then be sorted into the appropriate order to reconstitute the genome of the target subject (or portion of the genome of the target subject being investigated).

Sequence fragment data aligner 14 accomplished sorting of the fragments in O(n) time and space complexity by making use of special properties of the input array, i.e., the data in the array in non-sparse and the genome positions are uniformly distributed (or the distribution can be approximately empirically). Given these properties, Sequence fragment data aligner 14 employs an approach that uses the genome position field in the input array to determine the target position of an output array representing the re-sequenced data. Duplicate target positions due to n-fold coverage (which can over 30 times or more in conventional sequencing platforms) are handled by assigning either overflow buckets to each position or anterior assigning of multiple target slots in the output array for each genome position depending on the distribution of reads over the genome and the resulting probability of hitting an already occupied slot. Once every tuple in the input array has been written to the output array (or to an overflow bucket), the output array is read through in ascending order and each tuple is appended to the end of a final result array (and if necessary collecting tuples from overflow buckets during this process). Due to the low sparsity and uniform distribution properties, system 10 runs in O(n) time and space complexity and will do so for every input array with these properties.

System 10 may implement a method 20 of sorting the sequence fragment data. Method 20 begins with the step of letting A be an array of tuples of length n to be sorted, where each tuple is comprised of an integer defining the target position in the sorted array 22 (the target position will be referred to as the position in the subsequent content). Next, d is chosen as an integer defining the number of estimated duplicate positions 24. This parameter can be determined empirically and inferred by the targeted n-fold coverage of the NGS experiment (coverage means to target the biological creation of multiple matching read fragments per read position for increased accuracy). M then is defined as a map with an integer key standing for position and a list of size d containing empty tuples of same type as in A 26. An empty array A' of size A*d may then be allocated 28. An overflow map O of size 0 is then initialized 30 (meant to grow by appending) where key is position and value a list of tuples. Next, a loop over A is executed 32, starting from lowest index 1 to sizeof(A) as follows:

determine target index
    targetIndex=A[index].position
    if (A'[targetIndex] list has empty slots)
    Add tuple A[index] to list in A'[targetIndex]
    else
        add to O using A[index].position as key and A[index] as tuple An empty array A" of sizeof(A) holding the final result is then created 34 to serve as the final output array. A loop over A' starting from lowest index 1 to sizeof(A') is then executed 36:

if (A'[index] ! empty):
    copy all tuples in list of A'[index] to A" by appending
    if O contains entries at position A'[index].position:
        copy all tuples in list of O[index] to A" by appending After this run 1-6 A" will be sorted time and space complexity is O(n).

In case the statistical distribution of positions is not uniform, d has to be replaced by an estimator function D:={position=>number of expected tuples} returning the estimated tuples at a certain position. This function can be derived empirically. Time complexity of O(n) can always be guaranteed, space complexity of O(n) can only be guaranteed if the distribution of positions is not sparse which is the case for NGS re-sequencing data. Time complexity of O(n) and space complexity of O(n) provide tremendous cost savings on hardware and energy savings. As a result, the speed and efficiency of the computer processing of the sequence data is significant improved over conventional systems and the present system and method comprises an advancement in the computer processing of the sequence data itself.

The descriptions of the various embodiments of the present invention have been presented for the purposes of illustration, but are not intended to be exhaustive or limited to the embodiments disclosed. Many modification and variations will be apparent to those of ordinary skill in the art without departing from the scope and spirit of the described embodiments. The terminology used herein was chosen to best explain the principles of the embodiments, the practical application or technical improvement over the technologies found in the market place, or to enable others of ordinary skill in the art to understand the embodiments disclosed herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer system for Next Generation Sequencing (NGS), comprising:
   one or more computer processors;
   one or more computer readable storage media;
   computer program instructions, the computer program instructions being stored on the one or more computer readable storage media for execution by the one or more computer processors; and
   the computer program instructions including instructions to:
      generate, via a next generation sequencer, a raw sequence fragment data file, wherein the raw sequence fragment data file includes a plurality of unordered data fragments comprising target indexes and a first count of the number of unordered fragments, corresponding to respective genetic fragments of a genome sample;
      generate, via the next generation sequencer, a second count, wherein the second count is an estimate of positions in a first array having been assigned two or more unordered data fragments;
      generate, via the next generation sequencer, a first map, associated with the first array, with a position key and an associated list comprising the second count number of elements;
      generate, via the next generation sequencer, the first array of a size of at least the first count multiplied by the second count;
      generate, via the next generation sequencer, a second map, associated with a second array, with a position key and array values of lists of unordered data fragments;

determine, via the next generation sequencer, if target index locations of the first array are empty, wherein the target index locations are selected in order from a first unordered data fragment to a last unordered data fragment of the plurality of data fragments;

responsive to the target index locations being empty, append, via the next generation sequencer, associated unordered data fragments to the first map at the target index locations;

responsive to the target index locations not being empty, append, via the next generation sequencer, the associated unordered data fragments to the second map at the target index locations;

generate, via the next generation sequencer, a second array of a size of the first count;

append, via the next generation sequencer, non-empty elements of the first map to corresponding locations of the second array;

append, via the next generation sequencer, non-empty elements of the second map to corresponding locations of the second array; and output, via the next generation sequencer, the second array in O(n) time complexity and O(n) space complexity to a base-pair sequencer.

2. The computer system of claim 1, wherein a size of the output array is equal to the plurality of unordered data fragments to be sorted multiplied by a total number of duplicate positions assigned to the plurality of unordered data fragments.

3. The computer system of claim 1, further comprising instructions to:

estimate, via the next generation sequencer, the number of the duplicate positions if a statistical distribution of duplicate positions is not uniform.

4. The computer system of claim 1, wherein a position in the output array includes an overflow bucket if two or more unordered data fragments are assigned the same position.

5. The computer system of claim 4, wherein the program instructions to align, against the reference genome, the plurality of sorted data fragments in the output array further comprises instructions to:

assign, via the next generation sequencer, each of the plurality of fragments to an appropriate position in the output array or the overflow bucket associated with that position.

6. The computer system of claim 5, further comprising instructions to:

read, via the next generation sequencer, through each position in the output array and any overflow buckets associated with each position in ascending order and append each of the plurality of sorted data fragments assigned to each position in the output array and any overflow buckets associated with each position together in that order.

7. A computer-implemented method of aligning genomic sequence data to a reference genome, comprising:

generating, via a next generation sequencer, a raw sequence fragment data file, wherein the raw sequence fragment data file includes a plurality of unordered data fragments comprising target indexes and a first count of the number of unordered fragments, corresponding to respective genetic fragments of a genome sample;

generating, via the next generation sequencer, a second count, wherein the second count is an estimate of positions in a first array having been assigned two or more unordered data fragments;

generating, via the next generation sequencer, a first map, associated with the first array, with a position key and an associated list comprising the second count number of elements;

generating, via the next generation sequencer, the first array of a size of at least the first count multiplied by the second count;

generating, via the next generation sequencer, a second map, associated with a second array, with a position key and array values of lists of unordered data fragments;

determining, via the next generation sequencer, if target index locations of the first array are empty, wherein the target index locations are selected in order from a first unordered data fragment to a last unordered data fragment of the plurality of data fragments;

responsive to the target index locations being empty, appending, via the next generation sequencer, associated unordered data fragments to the first map at the target index locations;

responsive to the target index locations not being empty, appending, via the next generation sequencer, the associated unordered data fragments to the second map at the target index locations;

generating, via the next generation sequencer, a second array of a size of the first count;

appending, via the next generation sequencer, non-empty elements of the first map to corresponding locations of the second array;

appending, via the next generation sequencer, non-empty elements of the second map to corresponding locations of the second array; and outputting, via the next generation sequencer, the second array in O(n) time complexity and O(n) space complexity to a base-pair sequencer.

8. The computer-implemented method of claim 7, wherein:

a size of the output array is equal to the plurality of unordered data fragments to be sorted multiplied by a total number of duplicate positions assigned to the plurality of unordered data fragments.

9. The computer-implemented method of claim 7, further comprising:

estimating, via the next generation sequencer, the number of duplicate position if a statistical distribution of duplicate positions is not uniform.

10. The computer-implemented method of claim 7, wherein a position in the output array includes an overflow bucket if two or more sorted data fragments are assigned the same position.

11. The computer-implemented method of claim 10, further comprising:

assigning, via the next generation sequencer, each of the plurality of fragments to an appropriate position in the output array or an appropriate overflow bucket.

12. The computer-implemented method of claim 11, further comprising:

reading, via the next generation sequencer, through each position in the output array and any overflow buckets associated with each position in ascending order and append each of the plurality of sorted data fragments assigned positions each position in the output array and any overflow buckets associated with each position together in that order.

13. A computer program product for aligning genomic sequence data to a reference genome, the computer program product comprising one or more computer readable storage media and program instructions stored on the one or more computer readable storage media, the program instructions including instructions to:

generate, via a next generation sequencer, a raw sequence fragment data file, wherein the raw sequence fragment data file includes a plurality of unordered data fragments comprising target indexes and a first count of the number of unordered fragments, corresponding to respective genetic fragments of a genome sample;

generate, via the next generation sequencer, a second count, wherein the second count is an estimate of positions in a first array having been assigned two or more unordered data fragments;

generate, via the next generation sequencer, a first map, associated with the first array, with a position key and an associated list comprising the second count number of elements;

generate, via the next generation sequencer, the first array of a size of at least the first count multiplied by the second count;

generate, via the next generation sequencer, a second map, associated with a second array, with a position key and array values of lists of unordered data fragments;

determine, via the next generation sequencer, if target index locations of the first array are empty, wherein the target index locations are selected in order from a first unordered data fragment to a last unordered data fragment of the plurality of data fragments;

responsive to the target index locations being empty, append, via the next generation sequencer, associated unordered data fragments to the first map at the target index locations;

responsive to the target index locations not being empty, append, via the next generation sequencer, the associated unordered data fragments to the second map at the target index locations;

generate, via the next generation sequencer, a second array of a size of the first count;

append, via the next generation sequencer, non-empty elements of the first map to corresponding locations of the second array;

append, via the next generation sequencer, non-empty elements of the second map to corresponding locations of the second array; and output, via the next generation sequencer, the second array in O(n) time complexity and O(n) space complexity to a base-pair sequencer.

14. The computer program product of claim 13, wherein a size of the output array is equal to the plurality of unordered data fragments to be sorted multiplied by a total number of duplicate positions assigned to the plurality of unordered data fragments.

15. The computer program product of claim 13, further comprising instructions to:

estimate, via the next generation sequencer, the number of the duplicate positions if a statistical distribution of the duplicate positions is not uniform.

16. The computer program product of claim 13, wherein the program instructions to align, against the reference genome, the plurality of sorted data fragments in the output array further comprise instructions to:

assign, via the next generation sequencer, each of the plurality of fragments to an appropriate position in the output array or an appropriate overflow bucket.

17. The computer program product of claim 16, further comprising instructions to:

read, via the next generation sequencer, through each position in the output array and any overflow buckets associated with each position in ascending order and append each of the plurality of sorted data fragments assigned to each position in the output array and any overflow buckets associated with each position together in that order.

\* \* \* \* \*